US009060861B2

(12) United States Patent
Tozzi et al.

(10) Patent No.: US 9,060,861 B2
(45) Date of Patent: Jun. 23, 2015

(54) ANNULOPLASTY RING SYSTEM

(75) Inventors: Piergiorgio Tozzi, Lausanne (CH);
Ludwig Von Segesser, Lausanne (CH);
Daniel Hayoz, Villars-sur-Glane (CH);
Enzo Borghi, Budrio (IT)

(73) Assignee: CENTRE HOSPITALIER UNIVERSITAIRE VAUDOIS, Lausanne (CH)

( * ) Notice: Subject to any disclaimer, the term of this patent is extended or adjusted under 35 U.S.C. 154(b) by 0 days.

(21) Appl. No.: 13/635,700

(22) PCT Filed: Dec. 16, 2011

(86) PCT No.: PCT/EP2011/073052
§ 371 (c)(1),
(2), (4) Date: Sep. 18, 2012

(87) PCT Pub. No.: WO2012/084714
PCT Pub. Date: Jun. 28, 2012

(65) Prior Publication Data
US 2013/0013059 A1    Jan. 10, 2013

(30) Foreign Application Priority Data
Dec. 22, 2010  (EP) .................................... 10196656

(51) Int. Cl.
*A61F 2/24* (2006.01)

(52) U.S. Cl.
CPC .............. *A61F 2/2448* (2013.01); *A61F 2/2442* (2013.01); *A61F 2/2445* (2013.01); *A61F 2250/0002* (2013.01); *A61F 2250/0004* (2013.01)

(58) Field of Classification Search
CPC ... A61F 2/2442; A61F 2/2445; A61F 2/2448; A61F 2/2451; A61F 2/2409; A61F 2/2466; A61F 2/04; A61F 2/042; A61F 2/246
USPC ..................... 623/2.36–2.37, 2.14, 2.17, 2.18, 623/2.38–2.39, 23.65, 23.67
See application file for complete search history.

(56) References Cited

U.S. PATENT DOCUMENTS

| 5,064,431 A | 11/1991 | Gilbertson et al. |
| 7,713,298 B2 | 5/2010 | Shaulian et al. |
| 2007/0016287 A1* | 1/2007 | Cartledge et al. ............ 623/2.11 |
| 2009/0248148 A1 | 10/2009 | Shaolian |

FOREIGN PATENT DOCUMENTS

WO    2009126629 A1    10/2009

OTHER PUBLICATIONS

European Search Report dated Apr. 12, 2011, corresponding to the Foreign Priority Application No. EP 10 19 6656.

* cited by examiner

*Primary Examiner* — Andrew Iwamaye
*Assistant Examiner* — Leslie Lopez
(74) *Attorney, Agent, or Firm* — Young & Thompson

(57) ABSTRACT

An annuloplasty ring system for repairing an atrioventricular cardiac valve includes an external support ring (2), an inner adjustable ring (4), a sliding pushing element (6) mounted between the external and inner rings (2, 4), and actuating element designed to control the pushing element (6). The pushing element (6) is designed, when actuated by the actuating element, to slide between the external ring (2) and the inner ring (4) and to press on the inner ring (4) by using the external ring (2) as a support, in such a way that a precise part of the inner ring (4) is deformed without modifying the perimeter of the inner ring (4).

23 Claims, 4 Drawing Sheets

ANNULOPLASTY RING SYSTEM

TECHNICAL FIELD

The present invention relates to an annuloplasty ring system for repairing atrioventricular cardiac valves (such as mitral valve and tricuspid valve) to prevent backflow from the ventricles into the atrium during systole. In the interest of simplicity, the description of the invention is focused on mitral valve, but the concept, the function and the benefit apply to tricuspid valve also.

BACKGROUND OF THE INVENTION

Mitral annuloplasty relays on the implant of mitral ring having fixed shape and size. During the classical mitral valve repair procedure, the surgeon sizes the mitral annulus and chooses the mitral ring accordingly. This procedure is done on the arrested heart under cardiopulmonary bypass, which is not a physiologic condition. However, it is only after the weaning off the cardiopulmonary bypass that it is possible to assess the quality of the mitral repair. In other words, the surgeon has to wake up the patient to verify if he succeeded in the mitral repair. If the repair fails, the patient undergoes a second operation. Surgeons and cardiologists express a need in the possibility to adjust the ring after implantation. Having a mitral ring that changes its size after implantation and on a beating heart, could improve the quality of the mitral repair and overcome the annulus miss-sizing problem.

Some solutions have been found to reduce the risk of ineffective mitral annuloplasty.

U.S. Pat. No. 7,713,298 discloses an annuloplasty ring which comprises shape memory members configured to transform said annuloplasty ring from a first configuration having a first size of a ring dimension to other configurations having a size of the ring dimension, which is less than said first size. The shape memory members are responsive to changes in temperature and/or exposure to a magnetic field.

U.S. Pat. No. 5,064,431 discloses an adjustable annuloplasty ring for an orifice, comprising: a flexible fabric tube formed in the shape of a ring, means for dividing the tube into an inner channel and an outer channel which functions as a sewing flange by which the ring may be sutured to tissue surrounding the orifice, at least two drawstrings for adjusting the size and shape of the ring disposed in the inner channel, the drawstrings extending substantially around the circumference of the ring and having ends protruding from openings in the tube, each drawstring being coupled to the tube at least two separate anchor points. The size and shape of the ring may be adjusted by selectively tightening one or more ends of the drawstrings to constrict portions of the ring.

However, the drawback of such mitral rings is that their size can be adjusted only one time after implantation. Another drawback is that the ring, when adjusted, modifies its shape in such a way the ring becomes smaller, therefore the surface of the atrioventricular valve becomes smaller. This downsizing of the annulus could induce valve stenosis and has negative consequence on heart function.

US 2007/0016287 discloses an implantable device for controlling the shape and/or the size of an anatomical structure or lumen. The implantable device has an adjustable ring associated with drawstrings. When the drawstrings are tensioned, the ring is deformed. However, when the drawings are tensioned, a large zone of the ring is deformed. It is not possible to deform a precise part of the ring.

Therefore there are, at the present time, no adequate solutions, whether commercial or in the literature, for a mitral ring having a size which can be changed and adjusted several times after implantation and on a beating heart, on a regular basis.

SUMMARY OF THE INVENTION

The present invention provides an annuloplasty ring system for repairing an atrioventricular cardiac valve which allows to avoid the disadvantages of the prior art.

Accordingly, the present invention relates to an annuloplasty ring system comprising an external support ring, an inner adjustable ring, a sliding pushing element mounted between said external and inner rings, and actuating means designed to control said pushing element. The pushing element is designed, when actuated by the actuating means, to slide between the external ring and the inner ring and to push or press on the inner ring by using the external ring as a support, in such a way that a precise part of the inner ring is deformed without modifying the perimeter of the inner ring.

By moving the pushing element, the annuloplasty ring of the invention can be adjusted several times, on demand.

In the simplest embodiment of the invention, the actuating means may be designed to be manually activated.

In another embodiment, the actuating means may comprise a control unit and an actuator, which can comprise an electric motor or a shape memory alloy device.

Advantageously, the actuating means may be designed to allow a bidirectional movement of the pushing element.

The present invention relates also to an actuator for actuating a device, in particular for actuating an annuloplasty ring as described above, and comprising a shaft, a support, a cogwheel rotatably mounted on said support and linked to the device to be actuated, at least one hook designed to cooperate with said cogwheel, and at least one shape memory element, one of the support and the hook being designed to slide along said shaft with respect to the other when one is moved by at least one shape memory element changing its form, in order to generate a rotation movement of said cogwheel. In one embodiment, the support is movable along the shaft of the actuator, the hook being fixed. In another embodiment, the support is fixed and the hook is movable along the shaft of the actuator.

DETAILED DESCRIPTION

The present invention relates to an annuloplasty ring system especially for repairing regurgitating atrioventricular cardiac valves, such as mitral valve and tricuspid valve.

Figure 1:
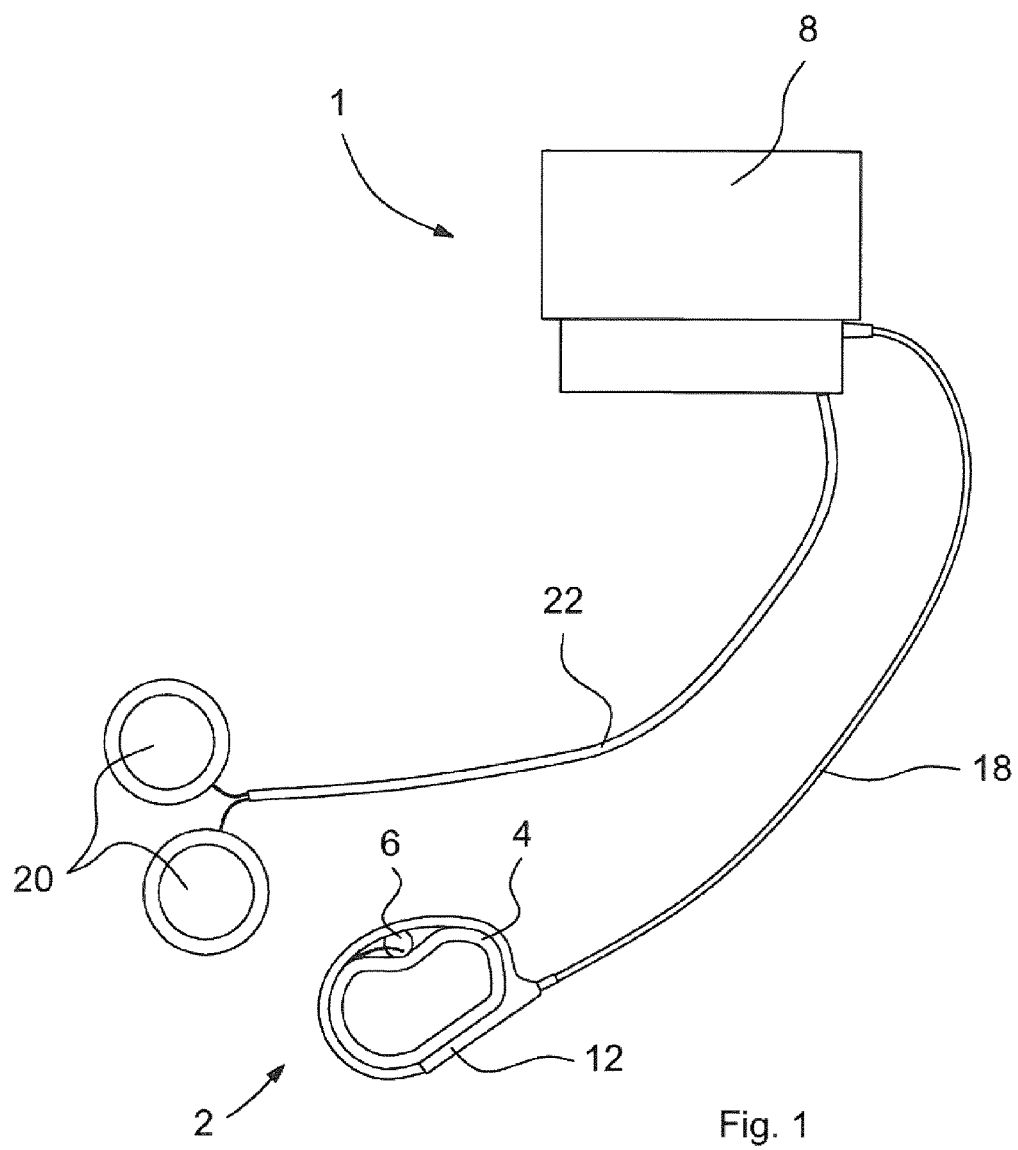
FIG. 1 is a schematic view of an embodiment of an annuloplasty ring according to the present invention.
Figure 2:
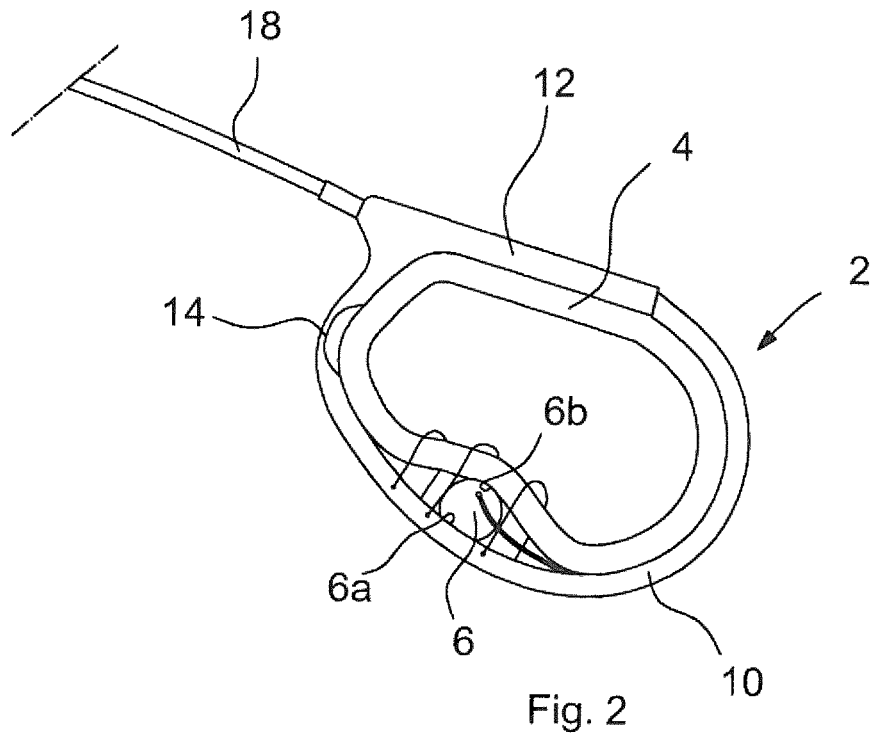
FIG. 2 is a detailed view of the ring of FIG. 1, the pushing element being in a first position.
Figure 3:
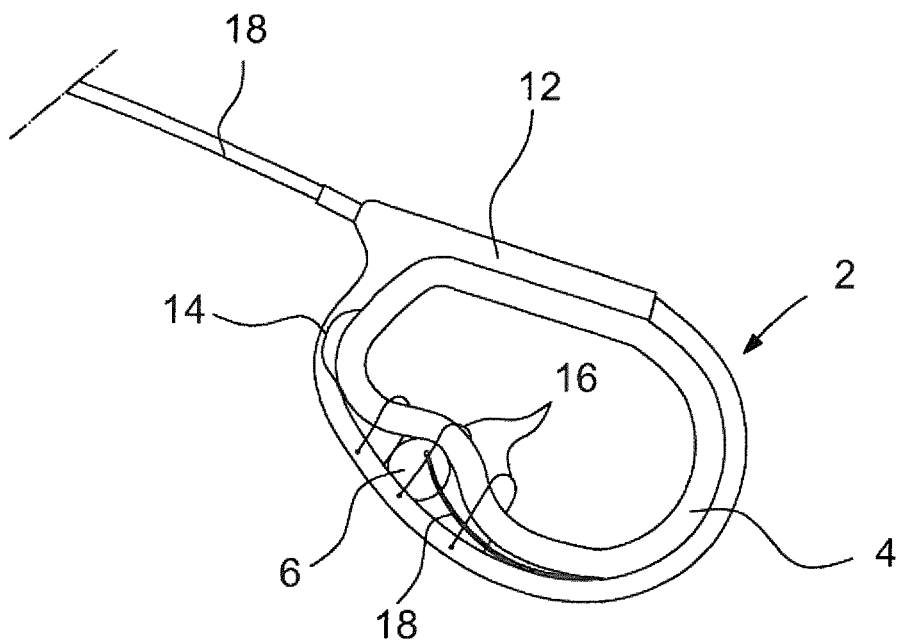
FIG. 3 is a detailed view of the ring of FIG. 1, the pushing element being in a second position.

FIGS. 1 to 3 shows an annuloplasty ring 1 comprising an external support ring 2, an inner adjustable ring 4, a pushing element 6 designed to slide between the external support ring 2 and the inner adjustable ring 4, and actuating means designed to control said pushing element 6.

Advantageously, the external ring 2 is rigid and not adjustable. Preferably, it may be made of rigid biocompatible material like a metallic material, as steel, gold or titanium, or polyether ether ketone (PEEK).

The external ring 2 is not fixed to the mitral annulus and only provides the support for the adjustment of the inner ring 4. This allows an extremely precise reshaping of the ring any time after its implant.

Advantageously, the external ring 2 may comprise an inner flange comprising a first part 10 on which the pushing element 6 is able to slide and a second part 12 to which the facing part of the inner ring 2 is fixed. Preferably, the external ring 2 may substantially have a D shape comprising a linear side corresponding to the second part 12 and a convex side corresponding to the first part 10.

Advantageously, the inner flange of the external ring 2 may comprise a recess 14 in which the pushing element 6 can be received, partially or completely, when it is in an initial position.

The inner ring 4 is preferably made of a flexible material, as biocompatible polymers, or may be a ring with a spring core.

The inner ring 4 is designed to be fixed to the mitral annulus using standard surgical technique.

The inner ring 4 comprises a linear part which is fixed to the linear part of the external ring 2 by any means known by one skilled in the art, as bonding or welding.

Several arches 16 may be mounted on the external ring 2 and around the inner ring 4 to avoid the overlapping of the two rings. The connection between each arch 16 and the external ring 2 allows the arch 16 to pivot or rotate with respect to the external ring 2 in such a way that the apex of the arch 16 always touches the inner ring 4.

Between the external ring 2 and the inner ring 4 is placed the pushing element 6. Advantageously, said pushing element 6 has a height greater than the distance between the external ring 2 and the inner ring 6 when it is not deformed in such a way that the pushing element 6 is still on contact with the external ring 2 and the inner ring 4. When the pushing element 6 is actuated and slides between said external and inner rings 2 and 4, it leans against the external rigid ring 2 and uses such external rigid ring 2 as a support to push, and more specifically to press on the inner flexible ring 4, and deform of precise part of said inner ring 4.

Advantageously, the pushing element 6 comprises a first surface 6a able to slide on the inner flange of the external ring 2 and a second surface 6b able to slide on the inner ring 4 and to push and press on it.

The pushing element 6 is activated by actuating means. In a preferred embodiment, said actuating means comprise transmission means linked to the pushing element 6 and able to move the pushing element 6 when said actuating means are actuated.

In some embodiments, the transmission means may be mechanical, by using a cable, hydraulic by using any fluid which is able to transmit to the pushing element a sliding movement.

Preferably, the transmission means may comprise a cable 18 linked to the pushing element 6. The end of the cable 18 is placed between the inner flange of the external ring 2 and the inner ring 4 and is connected to the pushing element 6.

Cable 18 may be protected by a coaxial sheath. The sheath can be made for example of polyimide, PTFE composites (PTFE and fluoroethylkene polymers), pure PTFE, or other appropriate polymers. Cables are well known in surgery. The cables can be made for example out of polyamide like Nylon®, polyether block amide, PTFE, or other appropriate polymers. Alternatively, other materials, as stainless steel or titanium, can be used. Surgeon is used to place cables in the human body.

In the embodiment as shown on FIG. 1, such actuating means may further comprise an actuator 8 and its control unit.

The actuating means are designed to provide the force to produce the deformation of the inner ring 4. The actuator 8 may comprise an electric motor or may comprise a shape memory alloy device.

Figure 4:
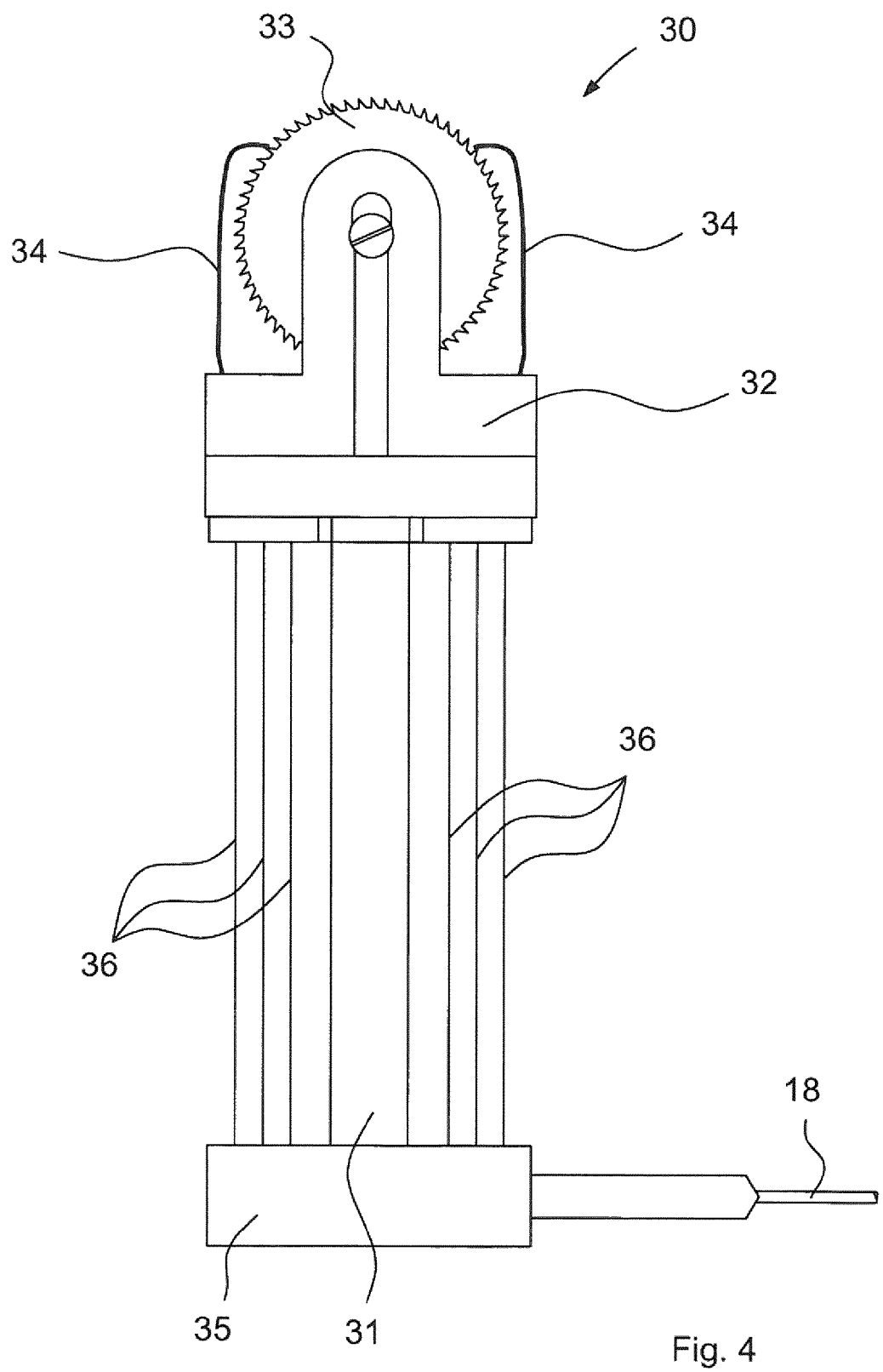
FIG. 4 shows an embodiment of an actuator usable with an annuloplasty ring of the invention.

FIG. 4 shows a possible embodiment of an actuator of the invention and comprising a shape memory alloy device.

Said actuator 30 comprises a hollow shaft 31 on which a sliding support 32 is mounted. A cogwheel 33 is rotatably mounted on said support 32. The cable 18 linked to the ring goes through the hollow shaft 31 and is connected to the cogwheel 33. The actuator comprises also two hooks 34, one designed to engage the teeth of the cogwheel 33 and generate the rotation of said wheel in one direction, the other being designed to prevent the rotation of said wheel in the opposite direction. The hooks 34 are fixed.

The actuator 30 comprises also at least one shape memory alloy (SMA) fiber 36 fixed to the support 32 and to a base 35 of the actuator. A suitable SMA material for the fibers is for example Nitinol™. In this case the fibers can be stretched by as much as 4% when below the transition temperature, and when heated, they contract, recovering thereby to their original, shorter length with a usable amount of force in the process. The mechanical characteristics are a function of the chemical composition and thermal processing. The transition temperature range varies according to the fiber's chemical composition and is usually comprised between 35° C. to 90° C. The Nitinol consists of about 50% Ni and 50% Ti. Such Nitinol wires and fibers are commercialized e.g. by Memry.

The fibers can have a spiral form in order to increase the length of the shortening.

Other particularly interesting materials are Biometal fibers (BMF) commercialized by Toki Corporation Inc., Japan (for example fibers BMX150 or BMF100). Those materials are able to reversibly contract upon a controlled heating caused by the supply of an electric current/voltage and can be repeatedly used several thousands of millions of times.

Such fibers are made for example of Ni—Ti—Cu alloy. For example, the composition ratios of Ni, Ti, and Cu are 46.9%, 44.8%, and 8.3%, respectively.

The rotation of the cogwheel 33 is generated by the activation of Nitinol fibers 36. Fiber's number depends on the pulling force required to displace the cogwheel 33. One fiber can generate a pulling force of about 100 g. When the fiber is activated, the cogwheel 33 moves towards the base 35, generating the clockwise rotation of the wheel thanks to the hooks 34. The clockwise movement of the wheel 33 produces the cable movement in backward direction.

Preferably, the control unit and the actuator 8 are placed away from the external and inner rings 2 and 4, for example in a box in the subcutaneous tissue.

The annuloplasty ring system further comprises a source of energy for the control unit. Said source of energy can be implantable or placed outside the body of the patient. An implantable source of energy may be a transcutaneously rechargeable battery. Such battery is for example a Lithium-Ion or Lithium Polymer rechargeable battery commercialized by GreatBatch and others.

In other embodiments, the source of energy may comprise subcutaneous electrical contacts 20 which are linked to the control unit by electrical wires 22. Such electrical contacts 20 are placed under the skin of the patient and energy is supplied from an external source of energy to the control unit via said electrical contacts 20, when needed.

Advantageously, the control unit may be controlled via a remote control unit using for example a telemetric coupling system, said remote control unit being placed outside the patient body.

In the simplest embodiment of the invention, the actuating means may be designed to be manually activated. For example, the actuating means may comprise a manually activated screw like system connected to the cable 18, in such a way that the pushing element 6 moves, via the cable 18, when said system is manually actuated.

Advantageously, the actuating means may be designed to allow a bidirectional movement of the pushing element.

In some embodiments comprising actuators, the actuating means may comprise a second cable placed between the inner flange of the external ring 2 and the inner ring 4, on the side opposite to the side on which the first cable 18 is placed. The second cable is linked to the opposite side of the pushing element and linked to a second actuator and to a second control unit, in such a way that the first cable moves the pushing element in one direction and the second cable moves the pushing element in the opposite direction. A third subcutaneous electrical contact may be provided to supply energy to the second control unit.

In other embodiments comprising actuating means which are manually activated, the pushing element is connected on each side to a cable. The two cables run parallel to the external ring and are connected to its actuator system. Pulling one cable at a time results in pushing element displacement backward and/or forward.

Figure 5:
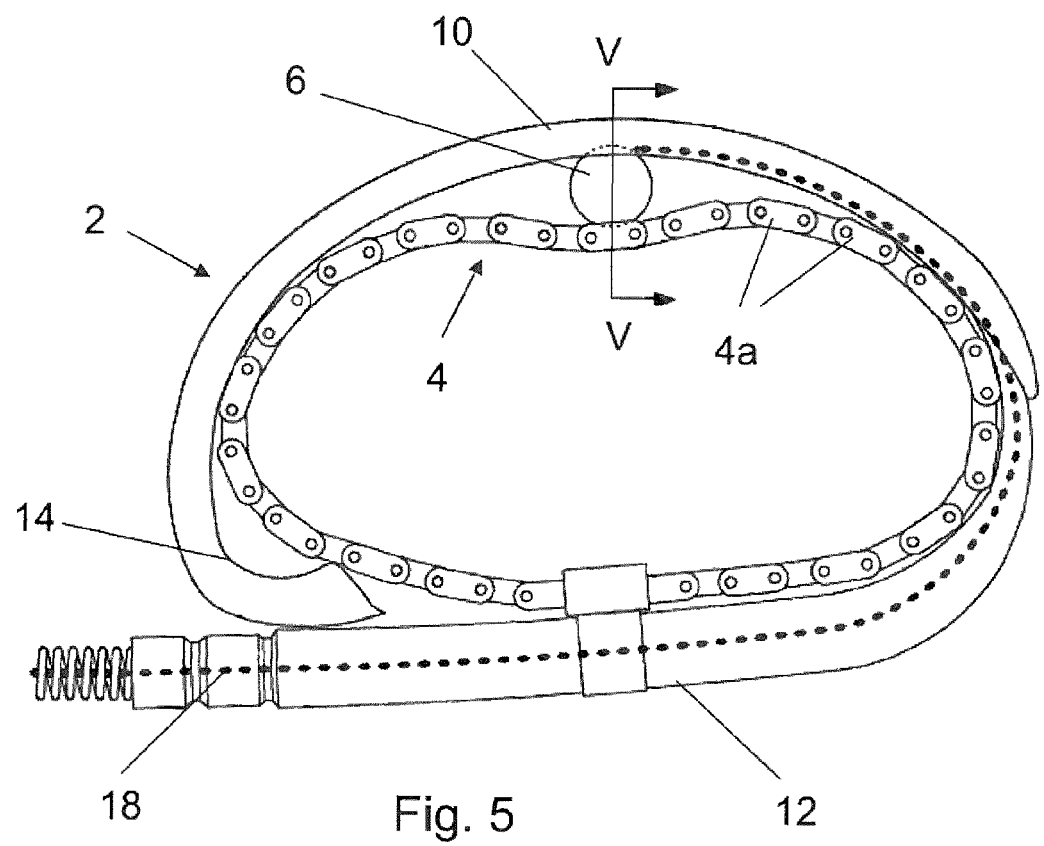
FIGS. 5 and 5a are respectively a view and a cross-sectional view of another embodiment of the ring.
Figure 5A:
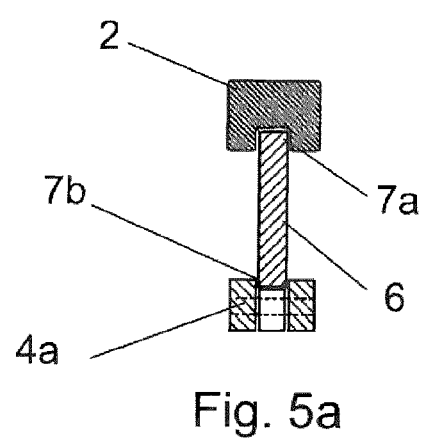

FIGS. 5 and 5a show another embodiment of the annuloplasty ring system of the invention. FIG. 5a is a cross-sectional view along V-V of FIG. 5.

In this embodiment, the inner ring 4 is a chain comprising links 4a which are articulated ones with respect to the others, in such a way that the chain is flexible. As the links 4a are articulated ones with respect to the others, this embodiment allows that a precise part of the inner ring 4 is deformed without deforming the other part of the inner ring.

Moreover, the external ring 2 and the chain comprise facing channels or grooves 7a, 7b in which the pushing element 6 slides, in such a way the pushing element is maintained between the external and the inner rings 2 and 4. Obviously, one skilled in the art can use in another embodiment a pushing element which comprises two lateral grooves able to receive a slide bar provided on the inner flange of the external ring 2 and on the facing flange of the inner ring 4.

The chain is protected by a coating (for example a silicone coating) and by a flexible sleeve (for example in Dacron®), such sleeve being fixed to the mitral annulus using standard surgical technique.

In another embodiment, which is not shown, the inner ring may be a spring. In a specific embodiment, the spring has a square spring having a quadrangular or rectangular cross-section. Inside the spring there is a metallic band that is free to move. With respect to round spiral spring, the square spiral spring allows the inner band to change its shape under the action of pressure if the pressure is applied to the thicker part of the band, but not if the pressure is applied to the thinner part of the band. This feature results in a mitral annulus that is easy deformed in one direction which is parallel to the valve plan but not in another direction, which is perpendicular to the valve plan.

The annuloplasty ring system of the invention is implanted with standard surgical technique currently used for mitral rings, by suturing the inner ring to the valve annulus. The suture lines run only over the inner ring 4. The inner ring 4 is adjusted at best. The annuloplasty ring is available in different sizes.

After the implantation of the ring, a specialized doctor, can change the geometry of the inner adjustable ring 4 by using the remote external control unit and activating the actuating means or by manually scrolling the cable positioned under the skin under local anesthesia. When the actuating means are activated, the pushing element 6 slides on the external ring 2 while pushing and pressing on the inner ring 4. When the pushing element 6 slides between the external rigid ring 2 and the inner deformable ring 4, the external ring 2 provides a support to the pushing element 6 in such a way that the pushing element 6 pushes and presses on the inner deformable ring 4 resulting in the changes in the shape of the inner ring 4, and therefore of the mitral annulus to which it is attached. Therefore, a precise part of the inner ring 4 is deformed without modifying the perimeter of the inner ring 4, such part of the inner ring 4 deforming a precise corresponding part of the mitral valve. This movement reduces the distance between the anterior and the posterior leaflets of the mitral valve improving valve coaptation. The mitral valve can then be reshaped and repaired. Moreover, since the perimeter of the inner ring 4 is not reduced, the risk of stenosis is low.

With the ring of the invention, the action of reshaping the mitral annulus is local and doesn't affect the entire annulus. Using the surgical classification of the mitral valve anatomy that identifies three parts of the posterior leaflet of the mitral valve called P1, P2 and P3, the pushing element is able to reshape the mitral annulus in P1 or P2 or P3 according to the need of the patient. As an example, when the pushing element pushes P2, the posterior leaflet of the mitral valve approaches the anterior leaflet increasing leaflets' coaptation and valve continence.

The pushing element can be pushed backward and forward as many times as necessary to find the optimal functioning of the valve.

More specifically, the doctor can reshape the mitral annuloplasty and verify the hemodynamic result in real time using standard echocardiography. If the ring is still not correctly adjusted, the doctor can move again the pushing element and find the best position. The doctor can adjust the form of the mitral ring during the operation, on arrested heart, on beating heart and even after the operation has been completed, on a beating heart. Such adjustments could be done any time after the surgical procedure and could be repeated as much as needed. The adjustments could be made during, or just after the surgical procedure or a long time after such a surgical procedure, for example in the case of a morphologic modification of the valve.

The invention claimed is:

1. An annuloplasty ring system for repairing an atrioventricular cardiac valve, comprising:
    an external support ring,
    an adjustable inner ring mounted interior to the external support ring,
    a pushing element mounted between said external support and adjustable inner rings against an initial precise part of the adjustable inner ring and against an initial precise part of the external support ring, and
    an actuator connected to said pushing element, operation of the actuator moving the pushing element from a first position against the initial precise parts of said external support and adjustable inner rings to a second position against further precise parts of the external support and adjustable inner rings, wherein the actuator is operative to move the pushing element to push the adjustable inner ring from the first position to the second position, the pushing element leaning against the external support ring and using the external support ring as a support, to push against the adjustable inner ring and thereby radially inwardly deform a portion of the adjustable inner ring between the initial precise part and the further precise part of the adjustable inner ring without reducing a perimeter of said adjustable inner ring and without adjusting the external support ring and with the adjustable inner ring having, at a given location, a first radial distance prior to deformation and having a second radial distance after deformation at the given location, the second radial distance being less than the first radial distance at the given location.

2. The annuloplasty ring system according to claim 1, wherein the adjustable inner ring is fixable to a mitral annulus.

3. The annuloplasty ring system according to claim 1, wherein the external support ring comprises an inner flange comprising a first part on which the pushing element is able to slide and a second part to which the inner ring is fixed.

4. The annuloplasty ring system according to claim 3, wherein the inner flange of the external support ring comprises a recess that receives the pushing element.

5. The annuloplasty ring system according to claim 1, wherein the external support ring is made of a rigid metallic material.

6. The annuloplasty ring system according to claim 1, wherein the adjustable inner ring is made of a flexible material.

7. The annuloplasty ring system according to claim 1, wherein the adjustable inner ring is a square spiral spring comprising a free inner band.

8. The annuloplasty ring system according to claim 1, wherein the adjustable inner ring is a chain comprising links which are articulated ones with respect to the others.

9. The annuloplasty ring system according to claim 8, wherein the external support ring and the chain comprise facing channels in which the pushing element slides.

10. The annuloplasty ring system according to claim 1, wherein the pushing element has a height greater than the distance between the external support ring and the adjustable inner ring.

11. The annuloplasty ring system according to claim 1, wherein the pushing element comprises a first surface able to slide on the external support ring and a second surface able to slide and press on the adjustable inner ring.

12. The annuloplasty ring system according to claim 1, wherein the actuator comprises transmission means linked to the pushing element and able to move the pushing element when actuated by the actuator.

13. The annuloplasty ring system according to claim 12, wherein the transmission means comprise a cable linking the pushing element to the actuator.

14. The annuloplasty ring system according to claim 1, wherein the actuator is manually activated.

15. The annuloplasty ring system according to claim 1, wherein the actuator comprises a control unit.

16. The annuloplasty ring system according to claim 15, wherein the actuator comprises a shape memory alloy device.

17. The annuloplasty ring system according to claim 16, wherein the shape memory alloy device comprises a support, a cogwheel rotatably mounted on said support and linked to a transmission means, at least one hook designed to cooperate with said cogwheel, one of the support and the hook being designed to slide along a shaft with respect to the other when one is moved by at least one shape memory element changing its form, in order to generate a rotation movement of said cogwheel.

18. The annuloplasty ring system according to claim 1, wherein the actuator is designed to allow a bidirectional movement of the pushing element.

19. The annuloplasty ring system according to claim 1, further comprising arches mounted to the external support ring and around an exterior surface of the adjustable inner ring, the arches being pivotable with respect to the external support ring.

20. The annuloplasty ring system according to claim 1, wherein the external support ring is made of one of the group consisting of rigid biocompatible steel, rigid biocompatible gold, and rigid biocompatible titanium.

21. The annuloplasty ring system according to claim 1, wherein the external support ring is made of rigid biocompatible polyether ether ketone (PEEK).

22. An annuloplasty ring system for repairing an atrioventricular cardiac valve, comprising:
    an external support ring, said external support ring being non-adjustable;
    an adjustable inner ring;
    a pushing element mounted between the adjustable inner ring and the external support ring with the pushing element located being against a radially outer part of the adjustable inner ring and against a radially inner part of the external support ring; and
    an actuator connected to said pushing element, operation of the actuator moving the pushing element from an initial first position between said external support and adjustable inner rings to a further second position between said external support and adjustable inner rings,
    wherein when the operation of the actuator moves the pushing element from the first position to the second position, the pushing element leans against the external support ring and, using the external support ring as a support to push against the adjustable inner ring, the pushing element radially inwardly deforms a portion of the adjustable inner ring between an initial precise part of the adjustable inner ring at the first position and a further precise part of the adjustable inner ring at the second position such that i) at a given location, the adjustable inner ring has a first radial distance prior to deformation and the adjustable inner ring has a smaller second radial distance after deformation at the given location, ii) a perimeter of the adjustable inner ring is not changed and iii) the external support ring is not adjusted.

23. The annuloplasty ring system for repairing an atrioventricular cardiac valve, comprising:
    an external support ring, having an exterior surface, the exterior surface of the external support ring having a radially inner perimeter and a radially outer perimeter;
    an adjustable inner ring, the adjustable inner ring having an exterior surface, the exterior surface of the adjustable inner ring having a radially adjustable inner perimeter and a radially outer perimeter, the radially outer perimeter of the exterior surface of the adjustable inner ring being mounted interior to and against the radially inner perimeter of the exterior surface of the external support ring;
    a pushing element mounted between and against an initial precise part of the radially outer perimeter of the exterior surface of the adjustable inner ring and against a part of the radially inner perimeter of the exterior surface of the external support ring; and an actuator, a terminal end of the actuator connected to said pushing element, operation of the actuator moving the pushing element from a first position against the initial precise part between said external support and adjustable inner rings to a second position at a new precise part against the radially outer perimeter of the exterior surface of the adjustable inner ring and against a new part of the radially inner perimeter of the exterior surface of the external support ring, wherein the actuator is operative to move the pushing element to push the adjustable inner ring from the first position to the second position, the pushing element leaning against the external support ring and using the external support ring as a support to push against the radially outer perimeter of the exterior surface of the adjustable inner ring and thereby radially inwardly deform a portion of the adjustable inner ring between the initial precise part and the new precise part of the adjustable inner ring without reducing a perimeter of the exterior surface of said adjustable inner ring and without adjusting the external support ring, and at a given location, the adjustable inner ring has a first radial distance prior to deformation and the adjustable inner ring has a second radial distance after deformation at the given location, the second radial distance being less than the first radial distance at the given location.

\* \* \* \* \*